(12) United States Patent
Kim et al.

(10) Patent No.: US 8,798,706 B2
(45) Date of Patent: Aug. 5, 2014

(54) LOOP STRUCTURES FOR SUPPORTING DIAGNOSTIC AND/OR THERAPEUTIC ELEMENTS IN CONTACT WITH TISSUE

(75) Inventors: Isaac Kim, San Jose, CA (US); Raj Subramaniam, Fremont, CA (US); Josef V. Koblish, Sunnyvale, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 777 days.

(21) Appl. No.: 12/561,527

(22) Filed: Sep. 17, 2009

(65) Prior Publication Data

US 2010/0087848 A1 Apr. 8, 2010

Related U.S. Application Data

(60) Provisional application No. 61/102,832, filed on Oct. 4, 2008.

(51) Int. Cl.
*A61B 5/042* (2006.01)
*A61B 18/14* (2006.01)

(52) U.S. Cl.
USPC .......... 600/374; 600/509; 600/393; 606/41

(58) Field of Classification Search
USPC .......... 600/374, 377, 372, 393, 509; 606/41
See application file for complete search history.

(56) References Cited

U.S. PATENT DOCUMENTS

| | | | |
|---|---|---|---|
| 5,290,295 A * | 3/1994 | Querals et al. .............. 623/1.23 |
| 5,910,129 A | 6/1999 | Koblish | |
| 6,315,778 B1 * | 11/2001 | Gambale et al. ................ 606/41 |
| 6,529,756 B1 | 3/2003 | Phan | |
| 6,542,781 B1 | 4/2003 | Koblish | |
| 6,645,199 B1 * | 11/2003 | Jenkins et al. ................. 606/41 |
| 6,702,811 B2 | 3/2004 | Stewart | |
| 6,711,444 B2 | 3/2004 | Koblish | |
| 6,745,080 B2 | 6/2004 | Koblish | |
| 7,740,629 B2 * | 6/2010 | Anderson et al. .............. 606/41 |
| 2002/0177765 A1 * | 11/2002 | Bowe et al. ................... 600/374 |
| 2007/0129721 A1 * | 6/2007 | Phan et al. ..................... 606/41 |
| 2008/0249518 A1 * | 10/2008 | Warnking et al. .............. 606/27 |
| 2009/0043186 A1 * | 2/2009 | Jung et al. .................... 600/374 |

FOREIGN PATENT DOCUMENTS

WO WO 98/49957 11/1998
WO WO 2005102199 A1 * 11/2005 ............ A61B 18/18

OTHER PUBLICATIONS

PCT International Search Report and Written Opinion dated Dec. 21, 2009 for PCT app. Ser. No. PCT/US2009/057267.

* cited by examiner

*Primary Examiner* — Lee S Cohen
*Assistant Examiner* — Erin M Cardinal
(74) *Attorney, Agent, or Firm* — Seager, Tufte & Wickhem, LLC

(57) ABSTRACT

An apparatus which includes a dual loop structure that carries a plurality of operative elements. A guide with a distal indentation that may be used to reorient a dual loop structure.

31 Claims, 12 Drawing Sheets

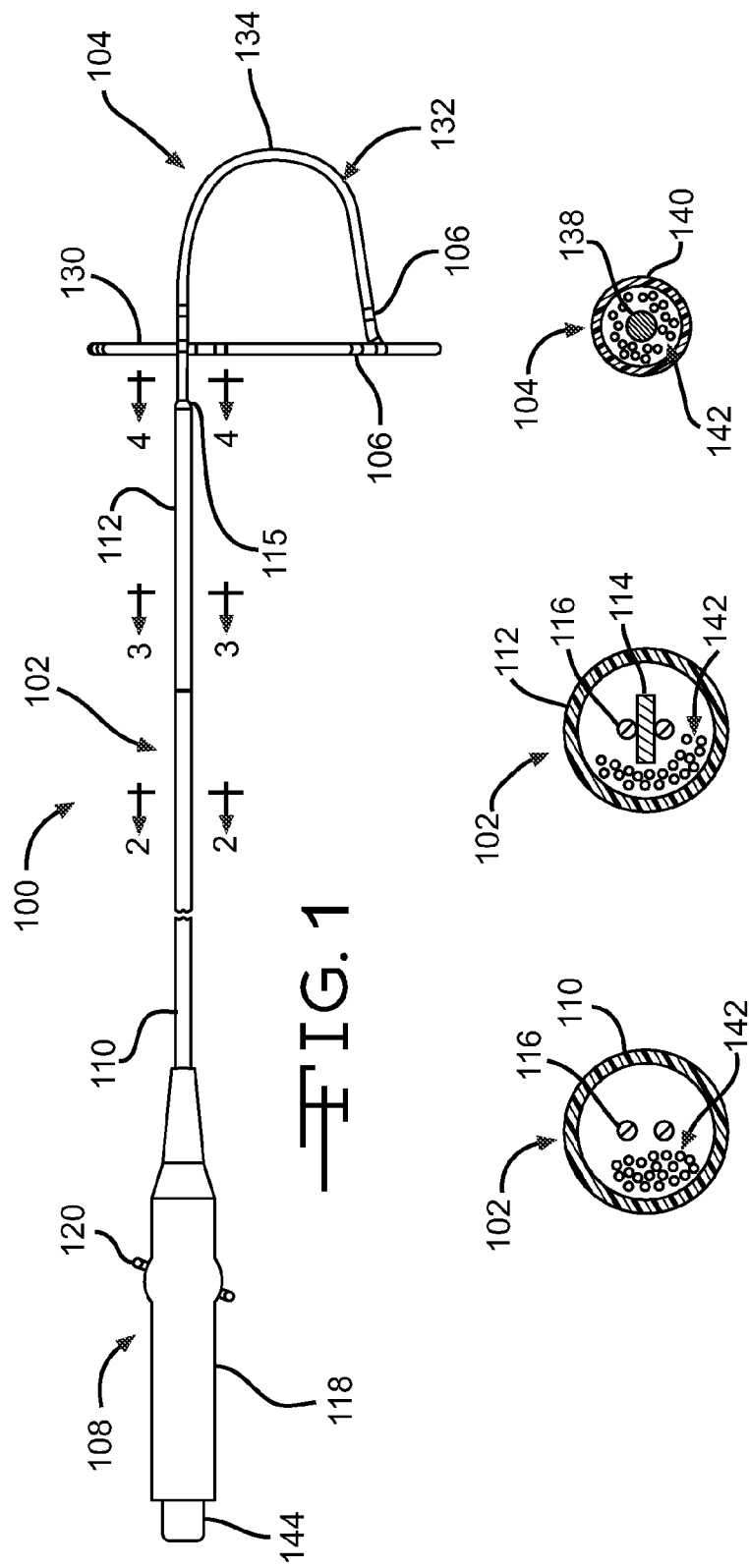

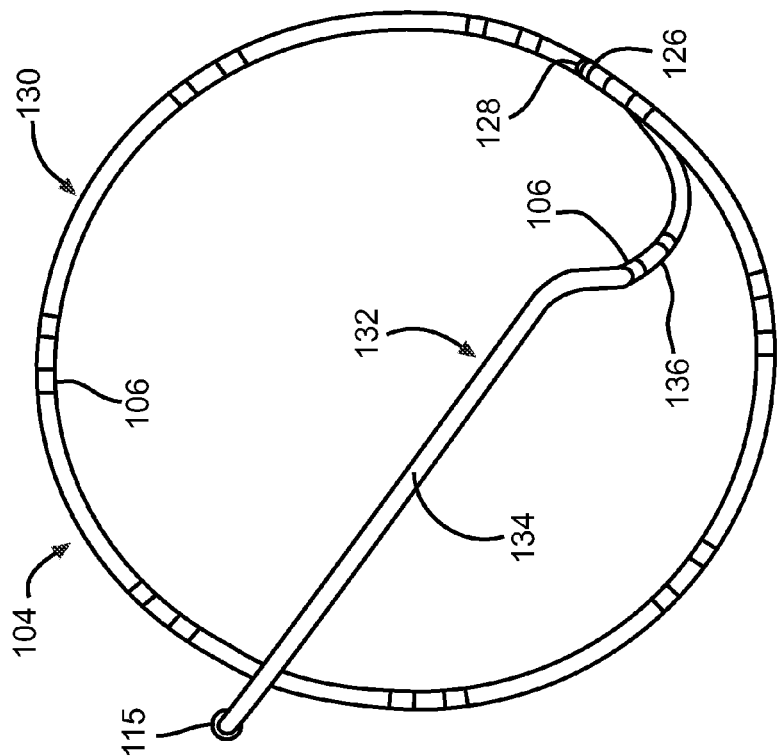
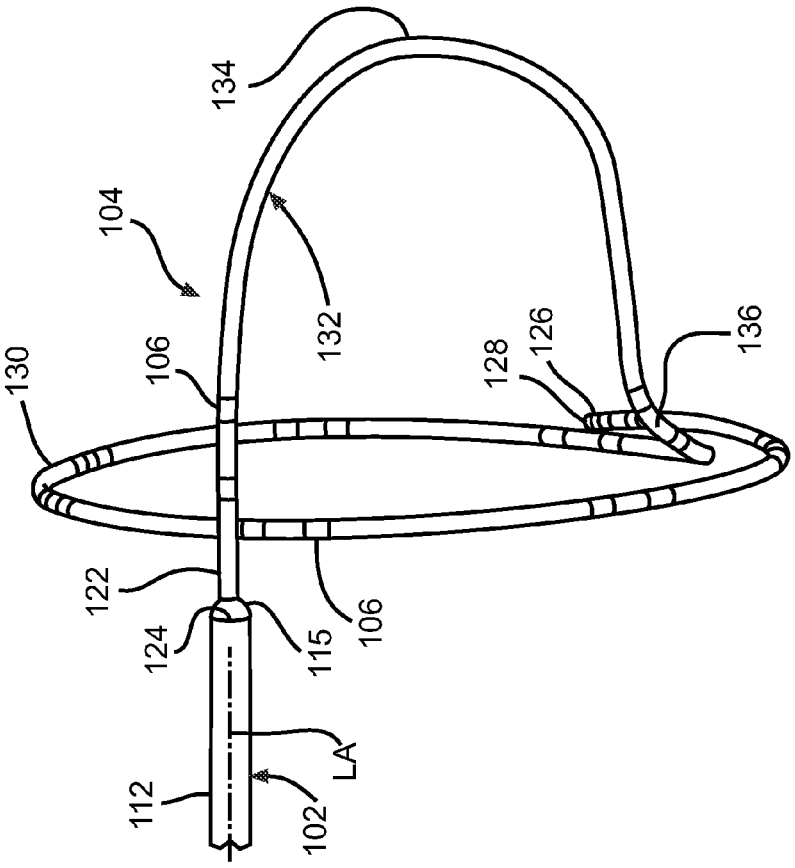

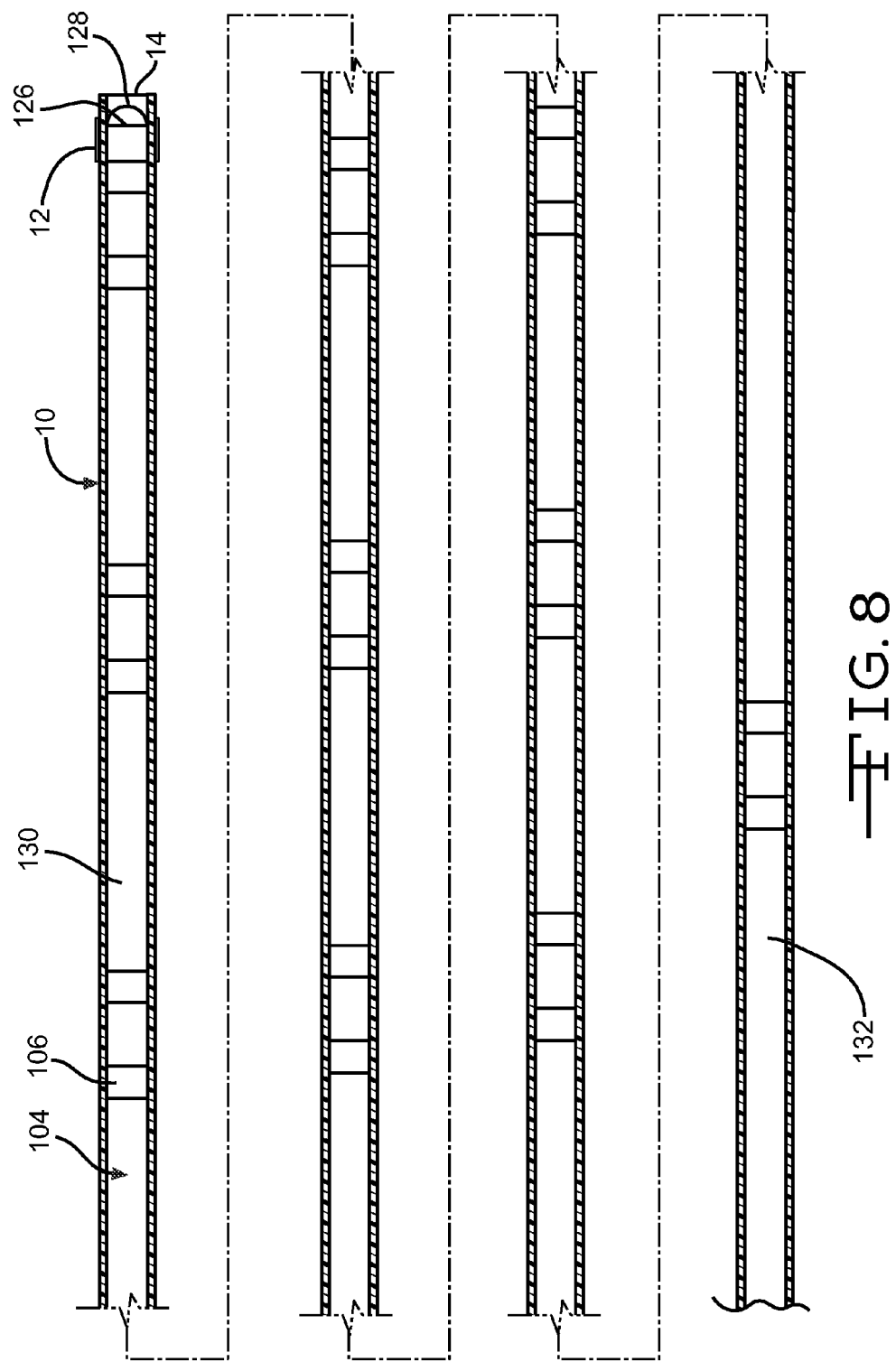

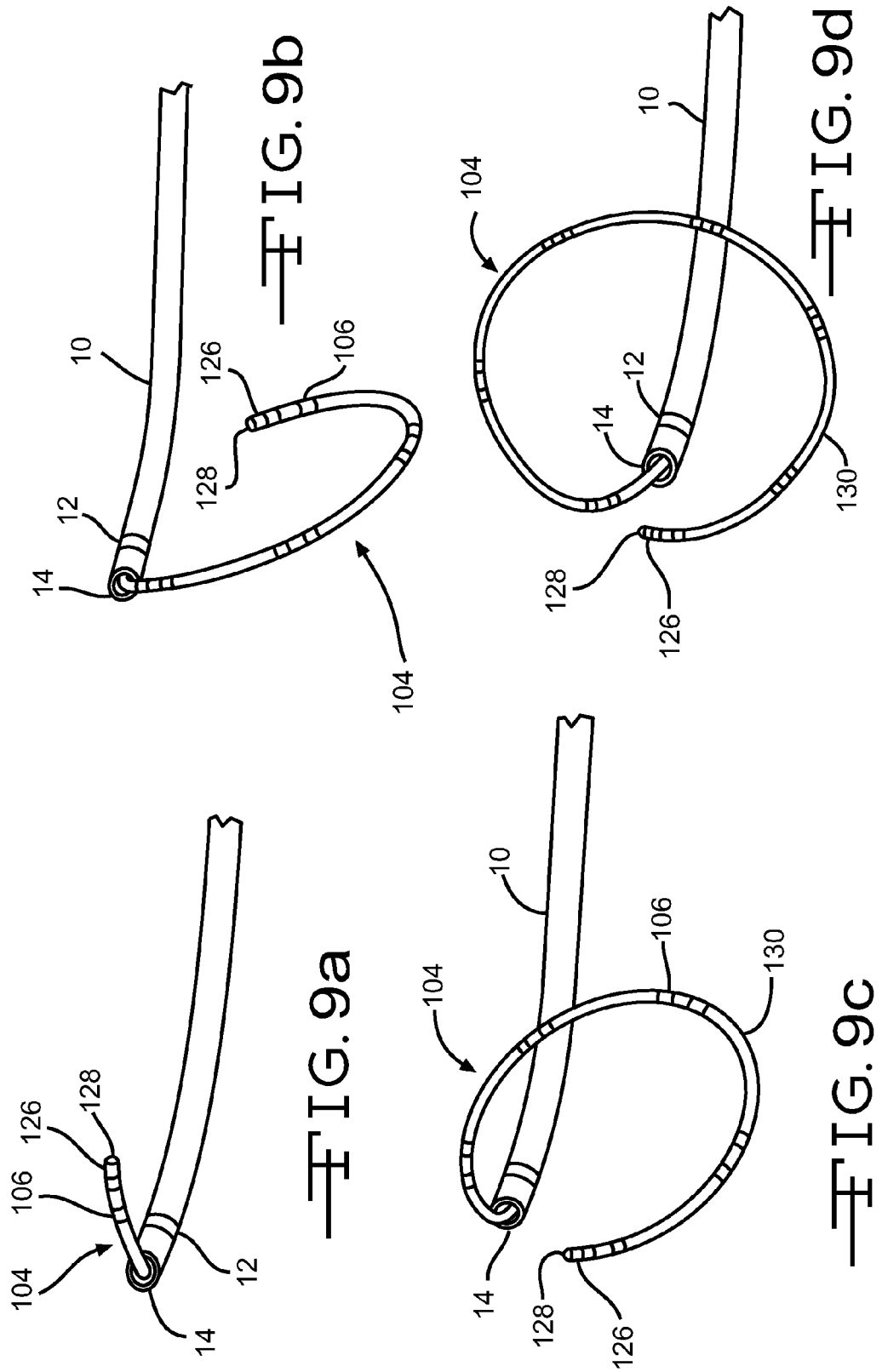

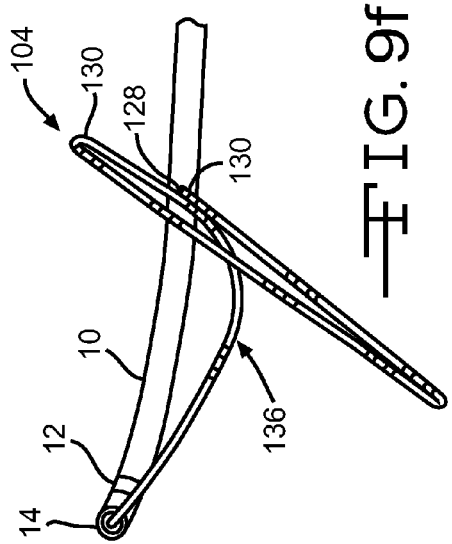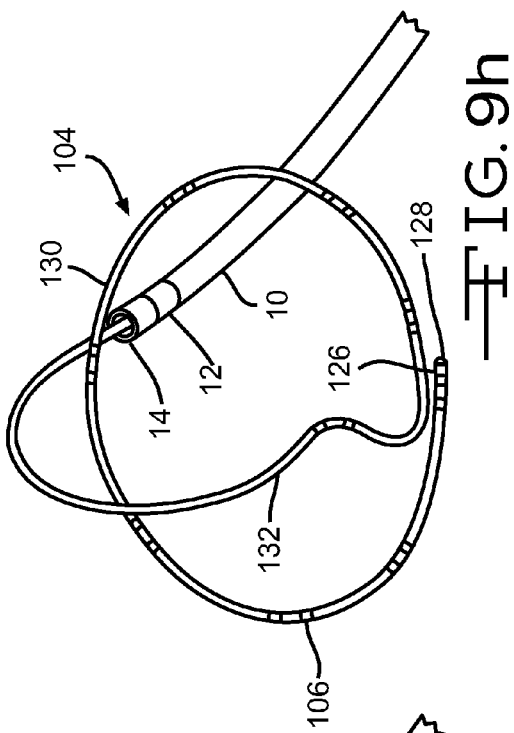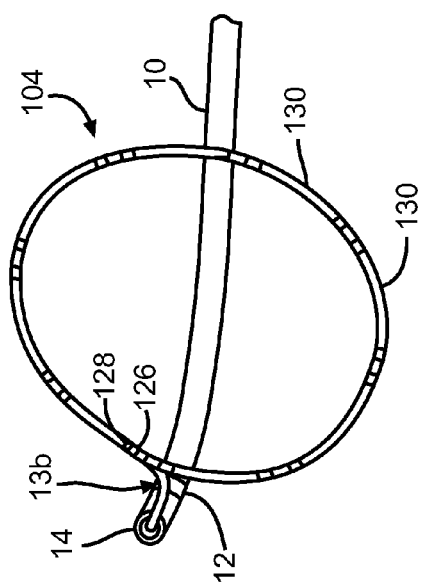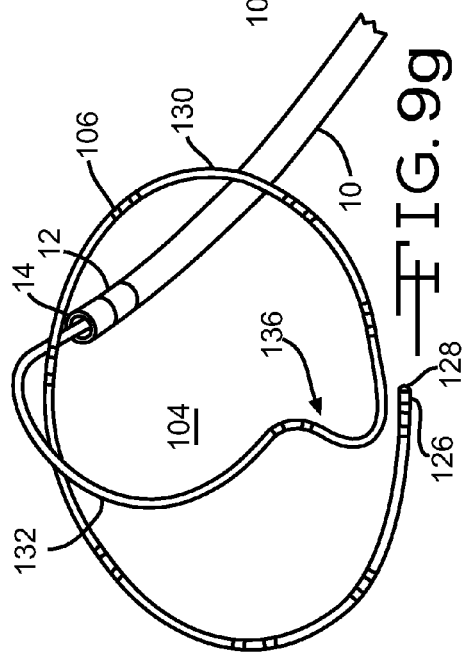

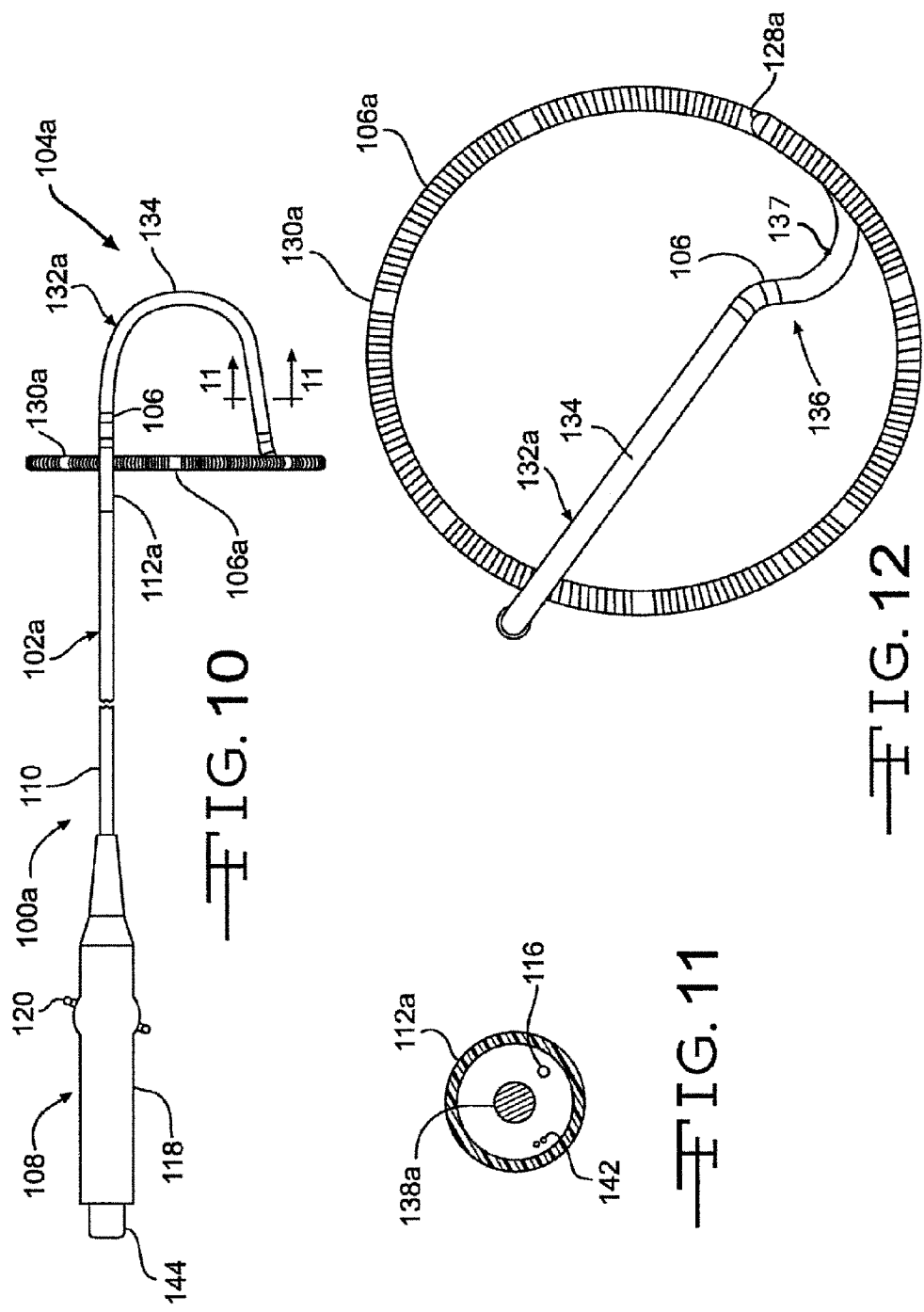

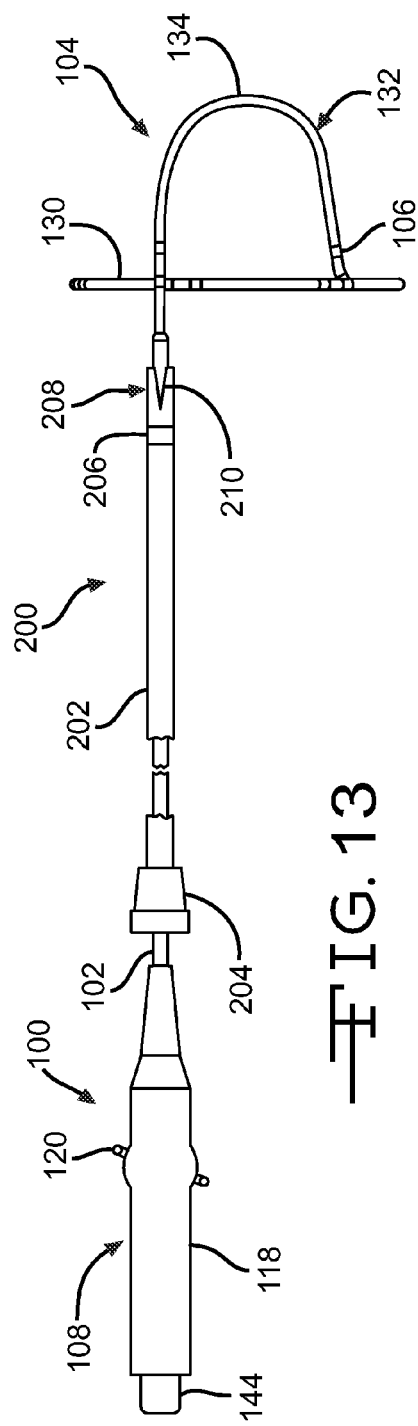
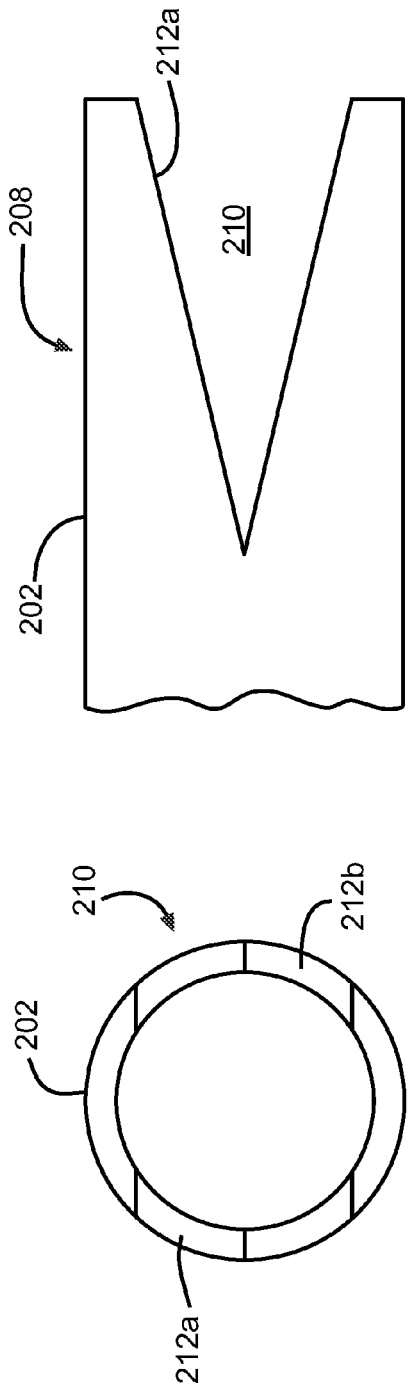
FIG. 13
FIG. 14b
FIG. 14a

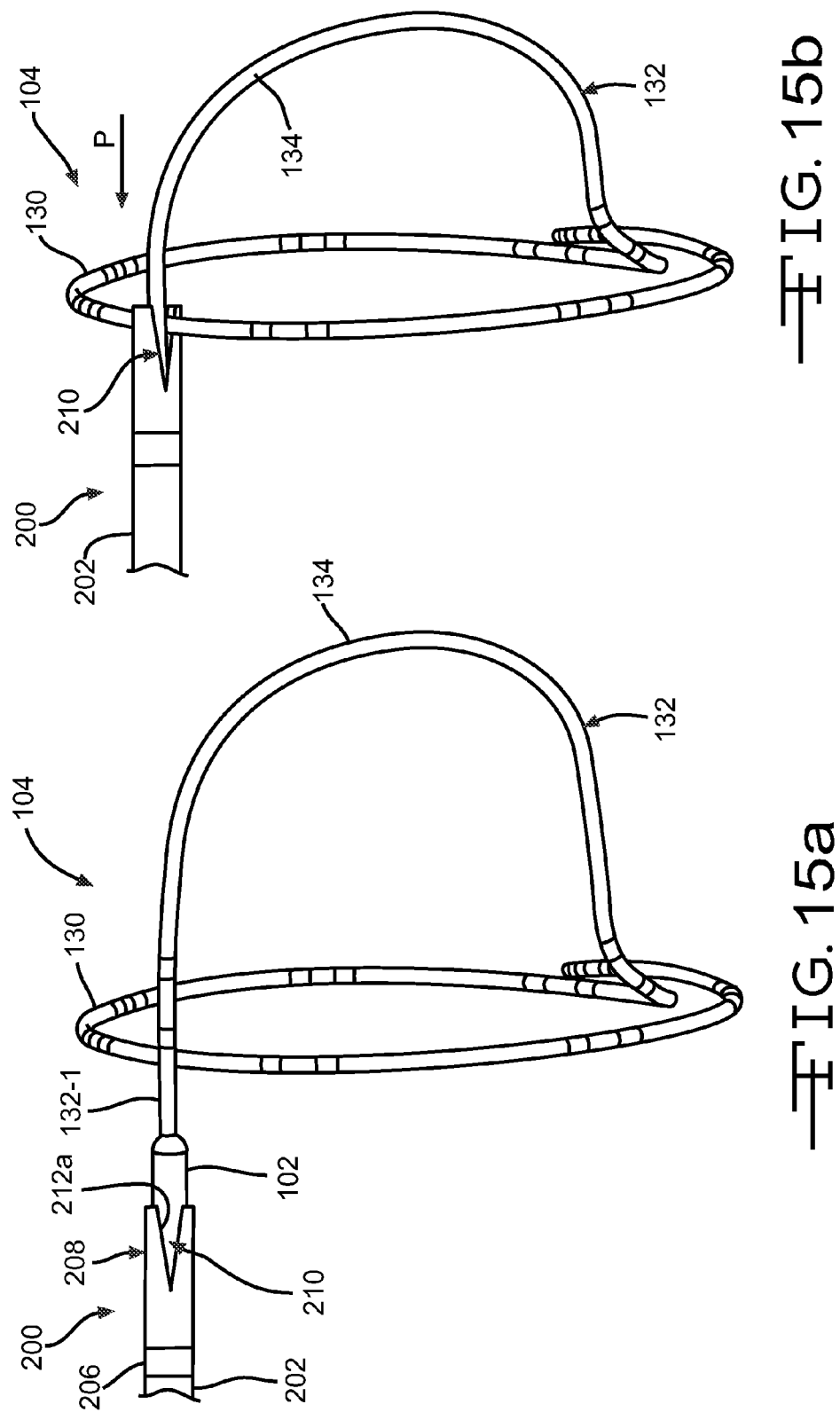

LOOP STRUCTURES FOR SUPPORTING DIAGNOSTIC AND/OR THERAPEUTIC ELEMENTS IN CONTACT WITH TISSUE

CROSS-REFERENCE TO RELATED APPLICATIONS

This application claims the benefit of U.S. Provisional Application Ser. No. 61/102,832, filed Oct. 4, 2008 and entitled "Loop Structures For Supporting Diagnostic and/or Therapeutic Elements in Contact With Tissue," which is incorporated herein by reference.

BACKGROUND

1. Field of Inventions

The present inventions relate generally to medical devices that support one or more diagnostic and/or therapeutic elements in contact with body tissue that is associated with, for example, body orifices or lumens.

2. Description of the Related Art

There are many instances where diagnostic and/or therapeutic elements (collectively "operative elements") must be inserted into the body to, for example, map and/or ablate body tissue. One instance involves the treatment of cardiac conditions such as atrial fibrillation, atrial flutter and ventricular tachycardia, which lead to an unpleasant, irregular heart beat, called arrhythmia. Atrial fibrillation, flutter and ventricular tachycardia occur when anatomical obstacles in the heart disrupt the normally uniform propagation of electrical impulses in the atria. These anatomical obstacles (called "conduction blocks") can cause the electrical impulse to degenerate into several circular wavelets that circulate about the obstacles. These wavelets, called "reentry circuits," disrupt the normally uniform activation of the chambers within the heart. Treatment of these cardiac conditions frequently involves mapping and ablation of tissue within the heart.

A variety of minimally invasive electrophysiological procedures employ catheters that position one or more operative elements adjacent to the target tissue region within the heart. Such catheters are relatively long and flexible shaft and carry the operative elements at or near their distal end. The proximal end of the catheter is connected to a handle which may or may not include steering controls for manipulating the distal portion of the catheter. The length and flexibility of the catheter allow the catheter to be inserted into a main vein or artery (typically the femoral artery), directed into the interior of the heart where the operative elements contact the tissue that is to be mapped and/or ablated. Fluoroscopic imaging may be used to provide the physician with a visual indication of the location of the catheter. Exemplary catheters are disclosed in U.S. Pat. Nos. 6,013,052, 6,203,525, 6,214,002 and 6,241,754.

One cardiac area that has proven difficult to treat with conventional catheters is the pulmonary veins. For example, ectopic atrial fibrillation may be cured by forming circumferential lesions in the antrum or ostium of pulmonary veins that include an arrhythmogenic foci. The portion of the catheter that carries the operative elements must be properly positioned relative to the pulmonary vein, and must remain in the proper position, for effective mapping and ablation of the pulmonary vein to proceed. The present inventors have determined that, with respect to positioning relative to a pulmonary vein, conventional catheters are susceptible to improvement.

SUMMARY

An apparatus in accordance with one embodiment of a present invention includes a body, which has a dual loop orientation with a first loop that is transverse to the longitudinal axis and a second loop that is transverse the first loop, and one or more operative elements on one or both of the loops.

An apparatus in accordance with one embodiment of a present invention includes a body, with the distal region being movable between a substantially linear orientation and a dual loop orientation including a proximal loop and a distal loop, the distal end of the body defining a portion of proximal loop, and one or more operative elements on one or both of the loops.

The present apparatus provide a number of advantages over conventional apparatus. For example, the present apparatus are self-orienting apparatus that may be used to position operative elements around the perimeter of a body lumen or orifice, such as a pulmonary vein, for diagnostic and/or therapeutic purposes, such as mapping and/or ablating tissue. The present apparatus may also be configured to wedge a portion thereof into a body lumen or orifice, such as a pulmonary vein, so as to prevent bodily movement, such as beating of the heart, from knocking the apparatus out of position.

The above described and many other features and attendant advantages of the present inventions will become apparent as the inventions become better understood by reference to the following detailed description when considered in conjunction with the accompanying drawings.

BRIEF DESCRIPTION OF THE DRAWINGS

Detailed description of embodiments of the inventions will be made with reference to the accompanying drawings.

FIG. 1 is a plan view of a catheter apparatus in accordance with one embodiment of a present invention.

FIG. 2 is a section view taken along line 2-2 in FIG. 1.

FIG. 3 is a section view taken along line 3-3 in FIG. 1.

FIG. 4 is a section view taken along line 4-4 in FIG. 1.

FIG. 5 is an enlarged view of the distal portion of the catheter apparatus illustrated in FIG. 1.

FIG. 6 is an end view of the distal portion of the catheter apparatus illustrated in FIG. 1.

FIG. 8 is partial section view showing the distal portion of the catheter apparatus illustrated in FIG. 1 in a straightened state.

FIGS. 9a-9i are perspective views showing the distal portion of the catheter apparatus illustrated in FIG. 1 being deployed.

FIG. 10 is a plan view of a catheter apparatus in accordance with one embodiment of a present invention.

FIG. 11 is a section view taken along line 11-11 in FIG. 10.

FIG. 12 is an enlarged view of the distal portion of the catheter apparatus illustrated in FIG. 10.

FIG. 13 is a plan view of a catheter apparatus and a guide in accordance with one embodiment of a present invention.

FIG. 14a is an end view of the guide illustrated in FIG. 13.

FIG. 14b is a side view of the distal portion of the guide illustrated in FIG. 13.

FIGS. 15a-15e are side views showing the distal portion of the catheter apparatus illustrated in FIG. 13 being deployed.

DETAILED DESCRIPTION OF EXEMPLARY EMBODIMENTS

Figure 7:
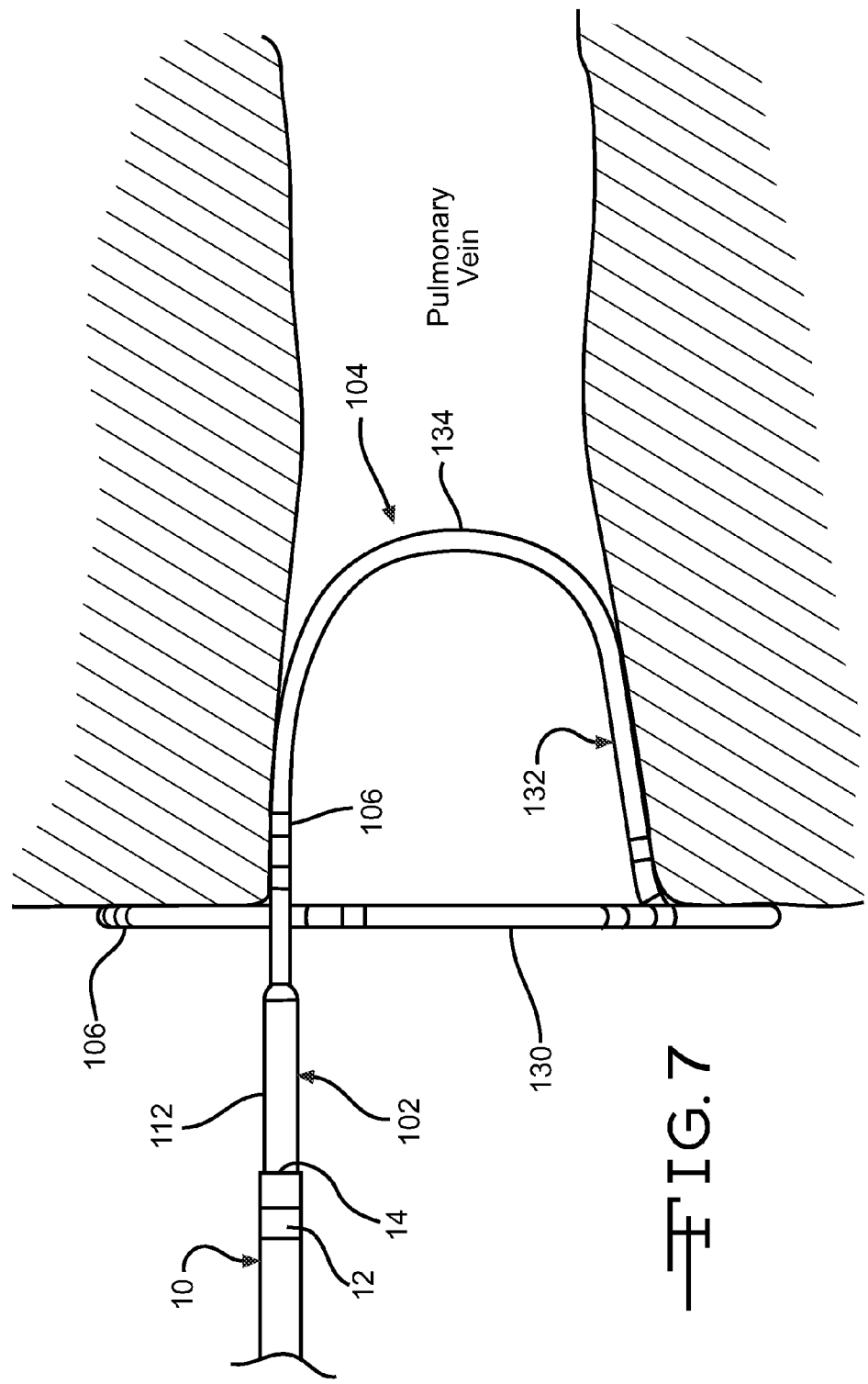
FIG. 7 is a side view showing the distal portion of the catheter apparatus illustrated in FIG. 1 deployed adjacent to a pulmonary vein.

The following is a detailed description of the best presently known modes of carrying out the inventions. This description is not to be taken in a limiting sense, but is made merely for the purpose of illustrating the general principles of the inventions.

The present inventions may be used within body lumens, chambers or cavities for diagnostic and/or therapeutic purposes in those instances where access to interior bodily regions is obtained through, for example, the vascular system or alimentary canal and without complex invasive surgical procedures. For example, the inventions herein have application in the diagnosis and treatment of arrhythmia conditions within the heart. The inventions herein also have application in the diagnosis or treatment of ailments in other regions of the body.

As illustrated for example in FIGS. 1-4, a catheter apparatus 100 in accordance with one embodiment of a present invention includes a catheter or other tubular body 102, a dual loop structure 104 that carries a plurality of electrodes or other operative elements 106, and a handle 108. The catheter 102 may be steerable and formed from two tubular parts, or members, both of which are electrically non-conductive. The proximal member 110 is relatively long and is attached to the handle 108, while the distal member 112, which is relatively short, carries the operative elements 106. The proximal member 110 may be formed from a biocompatible thermoplastic material, such as a Pebax® material (polyether block amide) and stainless steel braid composite or a polyethylene and stainless steel braid composite, which has good torque transmission properties. An elongate compression coil (not shown) may be provided within the proximal member 110. The distal member 112 may be formed from a softer, more flexible biocompatible thermoplastic material such as unbraided or fiber braided Pebax® material, polyethylene, or polyurethane. The proximal and distal members 110 and 112 may be either bonded together with an overlapping thermal bond or adhesively bonded together end to end over a sleeve in what is referred to as a "butt bond."

Although the present inventions are not so limited, the exemplary catheter 102 is configured for use within the heart and, accordingly, is about 3 French to about 8 French in diameter. Such a catheter may be about 60 cm to about 160 cm in length. The length and flexibility of the catheter 102 allow the catheter to be inserted into a main vein or artery (typically the femoral vein), directed into the interior of the heart, and then manipulated such that the dual loop structure 104 and operative elements 106 contact the target tissue.

With respect to steering, the exemplary catheter apparatus 100 illustrated in FIGS. 1-4 may be provided with a conventional steering center support and steering wire arrangement. The proximal end of the exemplary steering center support 114 is mounted near the distal end of the proximal member 110, while the distal end of the steering center support is secured to the support member 115. A pair of steering wires 116 are secured to opposite sides of the steering center support 114 and extend through the catheter 102 to the handle 108, which is also configured for steering. More specifically, the exemplary handle 108 includes a handle body 118 and a lever 120 that is rotatable relative to the handle body. The proximal end of the catheter 102 is secured to the handle body 118, while the proximal ends of the steering wires 116 are secured to the lever 120. Rotation of the lever 120 will cause the catheter distal member 112 to deflect relative to the proximal member 110. Additional details concerning this type of steering arrangement may be found in, for example, U.S. Pat. Nos. 5,871,525 and 6,287,301. Other suitable steering arrangements are disclosed in U.S. Pat. Nos. 6,013,052 and 6,287,301. Nevertheless, it should be noted that the present inventions are not limited to steerable catheter apparatus, or to any particular type of steering arrangement in those catheter apparatus which are steerable. For example, in a non-steerable implementation that is simply a modified version of the apparatus illustrated in FIGS. 1-4, the catheter distal member 112, steering center support 114, steering wires 116 and lever 120 may be omitted. The dual loop structure 104 in such an implementation may simply be carried on the distal end of a catheter 102 that does not include the more flexible distal member 112.

As illustrated for example in FIGS. 5, 6 and 8, the exemplary dual loop structure 104 has a proximal end 122, which is secured to the support member 115 or is otherwise associated with the distal end 124 of the catheter 102, and a distal end 126. As used herein, the "distal end" of a structure is the end of the structure that is distal-most when the structure is oriented in a straightened state with curves and/or bends removed therefrom (note FIG. 8). A "distal end" need not be the distal-most portion of a structure when the structure is in a bent, deflected or otherwise non-linear state. A tip member 128 may be mounted on the distal end of the exemplary dual loop structure 104.

The exemplary dual loop structure 104 includes a first loop 130 (or "proximal loop") that is transverse to the longitudinal axis LA (FIG. 5) of the catheter 102 and a second loop 132 (or "distal loop") that is transverse the first loop. At least a portion of the second loop 132 is distal of the first loop 130 and, the second loop 132 defines an apex 134 that is distal of the first loop 130. In the illustrated embodiment, the first loop 130 is perpendicular to catheter longitudinal axis LA (i.e. the first loop defines a plane that is perpendicular to the longitudinal axis) and the second loop 132 is perpendicular to the first loop (i.e. the second loop defines a plane that is perpendicular to the plane defined by the first loop). The relative orientation of the first loop 130 and the catheter longitudinal axis LA, and/or the relative orientation of the second loop 132 and the first loop, may be other than perpendicular in other implementations. The first and second loops 130 and 132 are also joined at an intersection 136.

Although not limited to any particular shape, the first loop 130 in the illustrated embodiment is an at least substantially full loop and is circular in shape. As used herein, an "at least substantially full loop" is a loop that extends about 330 degrees or more around the loop axis defined thereby. This number may be reduced slightly (e.g. to about 270 degrees) in those instances where the loop is adjustable and, after deployment, the loop can be adjusted such that it extends about 330 degrees or more around the loop axis. In the illustrated implementation, the first loop 130 extends slightly more than once, i.e. about 90 degrees more than once, around the loop axis defined thereby. With respect to shape, other suitable shapes include curved shapes such as an elliptical shape and non-curved shapes such as a square. The first loop 130 also defines an open area interior to the operative elements 106 through which blood or other bodily fluids can flow. As a result, the first loop 130 and operative elements 106 may be used to, for example, map and/or ablate tissue in or around the pulmonary vein, or other bodily orifice, without occluding fluid flow. This aspect of the exemplary dual loop structure 104 is discussed below with reference to FIG. 7.

Although not limited to any particular shape, the second loop 132 in the illustrated embodiment is an at least partial loop that may be semi-elliptical in shape. As used herein, an "at least partial loop" is a loop that has two portions which engage diametrically opposed regions of a pulmonary vein or other body lumen. Other suitable shapes for the second loop 132 include, but are not limited to, shapes with curves such as semi-circular and u-shapes. The second loop 132 could, alternatively, have a v-shape that would result in a pointed apex in place of the illustrated curved apex 134. The second loop 132 may be inserted into a body orifice, such as the pulmonary vein, to center or otherwise orient the first loop 130 relative to the body orifice. The second loop 132 may also be sized such that it will wedge itself into the pulmonary vein or other orifice in order to prevent bodily movement, such as beating of the heart, form knocking the dual loop structure 104 out of position. These aspects of the exemplary dual loop structure 104 is discussed below with reference to FIG. 7.

The dual loop structure 104 may, for example, include a center support 138 and an outer tubular member 140 (FIG. 4). The center support 138 may be a wire formed from resilient inert material, such as Nickel Titanium (commercially available under the trade name Nitinol) or 17-7 stainless steel wire that is configured to assume the dual loop configuration. The center support 138, which is secured to the support member 115 and to the loop structure tip member 128 in the illustrated embodiment, may also be housed in an insulative tube (not shown) formed from material such as polyester. Resilient injection molded plastic may also be used to form the center support 138. The cross-sectional shape of the center support 138 may circular (as shown), rectangular, or any other suitable shape. The outer tubular member 140 may be formed from an electrically non-conductive material such as Pebax® material or polyurethane.

The center support 138 in the exemplary dual loop structure 104 is heat set (or "pre-shaped") such that its relaxed orientation is the orientation illustrated in FIGS. 5 and 6. In other embodiments, the center support 138 may be formed from an actuatable material, such as actuator-type Nitinol that has a transition temperature above body temperature (typically between about 55° C. and 70° C.). When a heat-actuated material is heated to the transition temperature by, for example, supplying power to the operative elements 106 or passing current through the center support itself, the internal structure of the material dynamically changes and causes the material to contract and assume its heat-set shape, e.g. the shape illustrated in FIGS. 5 and 6.

The size of the dual loop structure 104 will depend upon its intended application. In the exemplary context of mapping and/or ablating tissue associated with pulmonary veins, the first loop 130 may be about 10 mm to about 50 mm in diameter, while the apex 134 of the second loop 132 may be located about 10 mm to about 30 mm from the first loop when the dual loop structure 104 is in the orientation illustrated in FIG. 5.

The operative elements 106 in the illustrated embodiments are electrodes. Other operative elements, such as lumens for chemical ablation, laser arrays, ultrasonic transducers, microwave electrodes, and ohmically heated hot wires, may be substituted for and/or used in combination with the electrodes.

The exemplary electrodes illustrated in FIGS. 5 and 6 are in the form of plurality of solid rings of conductive material such as silver, platinum, gold, stainless steel, plated brass, platinum iridium and combinations thereof. Alternatively, a conductive material, such platinum-iridium or gold, can be coated upon the appropriate portions of the dual loop structure 104 using conventional coating techniques or an ion beam assisted deposition (IBAD) process. For better adherence, an undercoating of nickel or titanium can be applied. Coils formed from electrically conducting material, like copper alloy, platinum, or stainless steel, or compositions such as drawn-filled tubing (e.g. a copper core with a platinum jacket) may also be used. The coils can be further coated with platinum-iridium or gold to improve its conduction properties and biocompatibility. The electrodes may also be in the form of helical ribbons or a conductive ink compound that is pad printed onto a non-conductive tubular body. A preferred conductive ink compound is a silver-based flexible adhesive conductive ink (polyurethane binder), however other metal-based adhesive conductive inks such as platinum-based, gold-based, copper-based, etc., may also be used to form electrodes. Such inks are more flexible than epoxy-based inks.

The number, size and spacing of the electrodes or other operative elements will depend upon the intended application of the underlying apparatus and the present inventions are not limited to any particular sizes and spacings. The electrode arrangement in the exemplary dual loop structure 104 is well suited for mapping. More specifically, and although not limited to any particular arrangement, there are eight pairs of electrodes on the first loop 130 and two pairs of electrodes on the second loop 132. The electrodes in each pair are about 1 mm in length with about 2 mm therebetween, and there is about 9 mm between adjacent pairs on the first loop 130. By way of example, but not limitation, in other exemplary arrangements, the number of electrode pairs may (or may not) be increased and the spacing between adjacent pairs decreased to, for example, 7 mm or 5 mm. The electrodes on the second loop 132 are positioned such that they will be in contact with tissue within the pulmonary vein. The diameter of the electrodes may range from about 2 French to about 4 French.

Another exemplary electrode arrangement is illustrated in FIGS. 10-12. The electrodes 106a on the first loop 130a are sized and spaced to be suitable for ablation as well as sensing. Here, the electrodes are in the form of helical coils. The coil electrodes may be about 2 mm to about 10 mm (as shown) in length with about 0.5 mm to 1 mm spacing, which will result in the creation of continuous a lesion pattern in tissue, i.e. a lesion pattern that extends from one electrode to another, when ablation energy is applied simultaneously to adjacent electrodes. The formation of such a lesion will, for example, electrically isolate the pulmonary vein from the left atrium. The electrodes on the second loop 132a are arranged in two pairs in the manner described above in the context of FIGS. 5 and 6. Other aspects of the exemplary embodiment illustrated in FIGS. 10-12 are discussed in greater detail below.

The electrodes 106 are electrically coupled to individual wires 142 (FIGS. 2-4). The wires 142 pass in conventional fashion through a lumen in the dual loop structure outer tubular member 140, as well as a lumen in the catheter 102, to an electrical connector 144 (e.g. a PC board, edge card connector, subminiature D connector, ribbon cable connector, or pin and socket connector) in the handle 108.

A plurality of temperature sensors (not shown), such as thermocouples or thermistors, may be located on, under, abutting the longitudinal end edges of, or in between, the electrodes or other operative elements in those instances where the operative elements are intended for ablation. Preferably, the temperature sensors are located at the longitudinal edges of the electrodes on the distally facing side of the first loop 130. In some embodiments, a reference thermocouple may also be provided. For temperature control purposes, signals from the temperature sensors are transmitted to the source of coagulation energy by way of wires (not shown) that are also connected to the aforementioned connector 144 on the handle 104.

The portion of the electrodes that are not intended to contact tissue (and intended to be exposed to the blood pool) may be masked through a variety of techniques with a material that is preferably electrically and thermally insulating. This prevents the transmission of ablation energy directly into the blood pool and directs the energy directly toward and into the tissue. For example, a layer of UV adhesive (or another adhesive) may be painted on preselected portions of the electrodes to insulate the portions of the electrodes not intended to contact tissue. Deposition techniques may also be implemented to position a conductive surface only on those portions of the dual loop structure 104 intended to contact tissue. Alternatively, a coating may be formed by dipping the electrodes in PTFE material. The electrodes may be covered with a porous material coating, which transmits coagulation energy through an electrified ionic medium. For example, as disclosed in U.S. Pat. No. 5,991,650, the electrodes may be coated with regenerated cellulose, hydrogel or plastic having electrically conductive components. With respect to regenerated cellulose, the coating acts as a mechanical barrier between the probe components, such as the electrodes, preventing ingress of blood cells, infectious agents, such as viruses and bacteria, and large biological molecules such as proteins, while providing electrical contact to the human body. The regenerated cellulose coating also acts as a biocompatible barrier between the catheter components and the human body, whereby the components can now be made from materials that are somewhat toxic (such as silver or copper). The porous material is saturated with ionic fluid (such as saline) prior to use.

The catheter apparatus 100 may be advanced though a conventional guide sheath or other tubular member 10 (FIGS. 7 and 8) to the target location. The tubular member 10 may be stiffer than the catheter 102 and dual loop structure 104 and be lubricious to reduce friction during movement of the apparatus 100. The tubular member 10 may also be provided with a radiopaque marker 12 and a relatively soft distal end 14 to prevent tissue trauma. The exemplary tubular member 10 is non-steerable and may be advanced over a guide wire (not shown) to the target tissue region in conventional fashion. Once the distal end 14 has reached the target tissue region, the guide wire may be withdrawn so that the catheter 102 and dual loop structure 104 may be inserted. Alternatively, a steerable tubular member may be provided. In either case, an introducer (not shown), such as those used in combination with basket catheters, may be used when introducing the dual loop structure 104 into the tubular member 10. Another exemplary tubular member is described below with reference to FIGS. 13-15e.

As illustrated in FIG. 8, the exemplary dual loop structure 104 will assume a generally straightened orientation (or "shape") while it is within the tubular member 10. The is may be accomplished by deflecting the dual loop structure 104 from its pre-set orientation to a straightened orientation in those instances where the relaxed orientation is that which is illustrated in FIGS. 5-7, or by simply not actuating the center support 138 in those instances where the center support is formed from an actuatable material such as actuator-type Nitinol. The dual loop structure 104 will, however, deflect as it advances through the vasculature. After the dual loop structure 104 has reached the target tissue region, the tubular member 10 may be moved proximally until the distal end 14 is proximal to the dual loop structure. The dual loop structure 104 may, alternatively, be advanced distally out of the tubular member 10. Once free of the compressive, straightening forces associated with the tubular member 10, the dual loop structure 104 will immediately return to its pre-shaped orientation, which is illustrated in FIGS. 5 and 6, or will return to the pre-shaped orientation when the center support is actuated. The electrodes or other operative elements 106 may then be positioned against the target tissue structure for the diagnostic and/or therapeutic procedure. Once the procedure is completed, the dual loop structure 104 may be withdrawn from the patient by way of the tubular member 10.

Figure 9I:
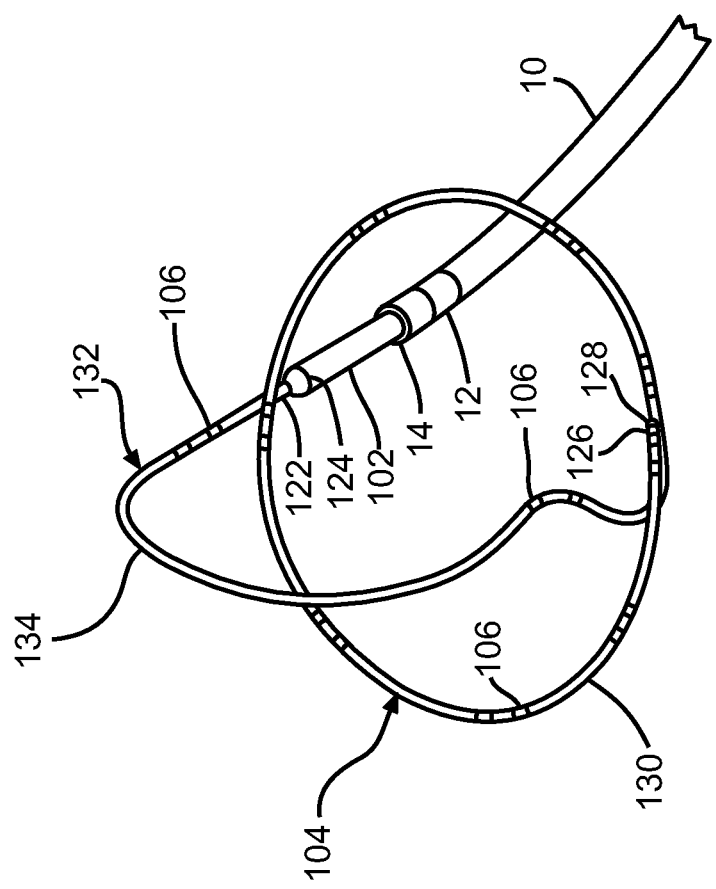

In those implementations where the exemplary dual loop structure 104 is configured to assume a pre-shaped orientation without actuation of the center support 138, the dual loop structure will transition from the straightened orientation (FIG. 8) to the relaxed pre-shaped orientation (such as that illustrated in FIGS. 5 and 6) in, for example, the manner illustrated in FIGS. 9a-9i. FIG. 9a shows the distal end of the exemplary dual loop structure 104 exiting the distal end 14 of the tubular member 10. As the distal portion of the straightened dual loop structure 104 advances beyond the distal end 14, the first loop 130 will take shape, as is shown in FIGS. 9b-9d. As the intersection 136 passes through the tubular member distal end 14, the first loop 130 will pivot proximally in the manner illustrated in FIG. 9e. The proximal portion of the straightened dual loop structure 104, as is illustrated in FIGS. 9f-9i, then passes through the tubular member distal end 14 to form the second loop 132 and complete the transition to the dual loop orientation. It should be noted here that the distal portion of the straightened dual loop structure 104 becomes the proximal portion (i.e. the first loop 130), and the proximal portion of the straightened dual loop structure becomes the distal portion (i.e. the second loop 132), when dual loop structure transitions from the straightened orientation (FIG. 8) to the dual loop orientation (FIG. 9i).

There are a variety of advantages associated with the present dual loop structures' ability to transition from the straightened orientation illustrated in FIG. 8 to the dual orientation illustrated in FIGS. 5 and 6. By way of example, by not limitation, the present dual loop structure is capable of forming first and second loops from a linear structure without the use of additional collapsible secondary structures that are mounted, on and extend radially outwardly from, a catheter or other linear device. Such collapsible secondary structures include hoops supported on splines, splines that extend radially outward, baskets, inflatable structures and the like, and may be configured to expand when advanced distally of a sheath or other tubular member, or when actuated by the clinician. Such secondary structures add complexity and cost to the overall apparatus. The present the present dual loop structure is also a single, unitary device that is capable of forming first and second loops, which is more efficient than using two separate devices (which may or may not pass through a common sheath or tube) to form first and second loops.

Other advantages associated with the present dual loop structures' are associated with the use thereof. As illustrated for example in FIG. 7, and in the exemplary context of mapping a pulmonary vein, the apparatus 100 may be moved distally after the dual loop structure 104 is free of the tubular member 10 until the second loop 132 is in the pulmonary vein and the first loop 130 is pressed against, and extends around, the pulmonary vein ostium. The second loop 132 centers the first loop 130 relative to the pulmonary vein, thereby insuring accurate positioning. The second loop 132 may also be size such that it is slightly larger that the pulmonary vein when in its relaxed orientation. As such, the second loop 132 will be compressed within, and with frictionally engage inner surface of, the pulmonary vein. The frictional engagement will keep the dual loop structure 104 in place and prevent bodily movement, such as beating of the heart, from knocking the apparatus out of position.

The present invention are, of course, not limited to the exemplary apparatus described above in the context of FIGS. 1-9i. By way of example, but not limitation, another exemplary catheter apparatus is generally represented by reference numeral 100a in FIGS. 10-12. The catheter apparatus 100a is also similar to the catheter apparatus 100 and similar elements are represented by similar reference numerals. The exemplary catheter apparatus 100a is, however, a non-steerable apparatus. Also, instead of a dual loop structure (e.g. dual loop structure 104) that extends axially (in the straightened state) from the distal end of a catheter, the distal portion of the catheter apparatus 100a is itself configured to move from a straightened orientation to a dual loop orientation. To that end, the exemplary catheter apparatus 100a includes a catheter 102a with a proximal member 110 and distal member 112a. A center support 138a, which is pre-shaped to a dual loop orientation in the manner described above, extends through the distal member 112a. One end of the center support 138a is secured to the catheter 102a at the distal end of the proximal member 110 and the other end of the center support is secured to a distal tip member 128a. The distal member 112a assumes a generally straightened shape while it is being advanced through a sheath or other tubular member, and will return to its pre-shaped dual loop orientation (FIGS. 10 and 12) when distal of the tubular member, in the manner described above with reference to the exemplary dual loop structure 104. With respect to the operative elements, and as noted above, the first loop 130a supports a plurality of relatively long, flexible electrodes 106a that are sized and spaced so as to be capable of forming a continuous lesion around a tissue (e.g. a pulmonary vein ostium) that is in contact with the first loop. The second loop 132a supports a two pairs of electrodes 106 that may be used in the manner described above.

Dual loop structures may also be configured such that the size (e.g. diameter) of the first loop is adjustable. One example an apparatus with an adjustable first loop is the catheter apparatus 100a. One end of a wire 116 is secured to the catheter 102a at the distal tip member 128a. The other end of the wire 116 is secured to the lever 120 on the handle 108. The lever 120 may be used to pull the wire 116 proximally, which causes the first loop 130a in the loop structure 104a to contract from its pre-shaped size. The first loop 130a will expand back to its pre-shaped size when the wire 116 is allowed to move distally due to rotation of the lever 120. For example, the elongate compression coil (not shown) discussed above in the context of the proximal member 110 may be extended through the portion of the loop structure 104a that forms the second loop 132a. The distal end of the coil would be located where the first loop structure 130a begins, i.e. just distal of the intersection 136 at point 137 (FIG. 12).

The exemplary catheter apparatus 100 (FIGS. 1-9i) may also be provided with the ability to adjust to the first loop 130. Here, one end of a wire (not shown) may be secured to the tip member 128. The other end may be secured to a device (not shown), such as a lever or slider, on the handle 108 to allow the clinician to pull the wire proximally.

Referring again to FIGS. 5-7 and 9i, the portion of the second loop 132 that extends proximally beyond the first loop 130 will be located outside the first loop after the dual loop structure 104 has been deployed (e.g. through tubular member 10) absent additional manipulation by the physician. There is a similar relationship between the loops 130a and 132a of the dual loop structure illustrated in FIGS. 10-12. The associated diagnostic or therapeutic procedure may be performed with the dual loop structure in this orientation (note FIG. 7). Alternatively, the clinician may desire to reorient the dual loop structure such that the portion of the second loop 132 that extends proximally beyond the first loop 130 will be located inside the first loop.

One example of a guide that may be used to reorient a dual loop structure after it has been deployed adjacent to a target tissue region is generally represented by reference numeral 200 in FIG. 13. The exemplary guide includes a sheath or other tubular member 202 and a handle 204. The tubular member 202 has an inner lumen configured to receive the catheter 102 and dual loop structure 104, may be stiffer than the catheter and dual loop structure, and may be lubricious to reduce friction during movement of the apparatus 100. The tubular member 202 may also be provided with a radiopaque marker 206 and a relatively soft distal region 208 to prevent tissue trauma. The distal region 208 includes an indentation 210, which extends proximally from the distal end of the tubular member 202, and may be used to hold a portion of the dual loop structure 104 during manipulation thereof, as is described below with reference to FIGS. 15a-15e. Although not limited to any particular shape, the indentation 210 has a V-shape in the illustrated implementation and is formed by a pair of diametrically opposed V-shaped cut-outs 212a and 212b in the tubular member wall (FIGS. 14a and 14b).

The exemplary tubular member 202 is non-steerable and may be advanced over a guide wire (not shown) to the target tissue region in conventional fashion. Once the distal end has reached the target tissue region, the guide wire may be withdrawn so that the catheter 102 and dual loop structure 104 may be inserted. Alternatively, a steerable tubular member may be provided. In either case, an introducer (not shown), such as those used in combination with basket catheters, may be used when introducing the dual loop structure 104 into the tubular member 202.

Figure 15C:
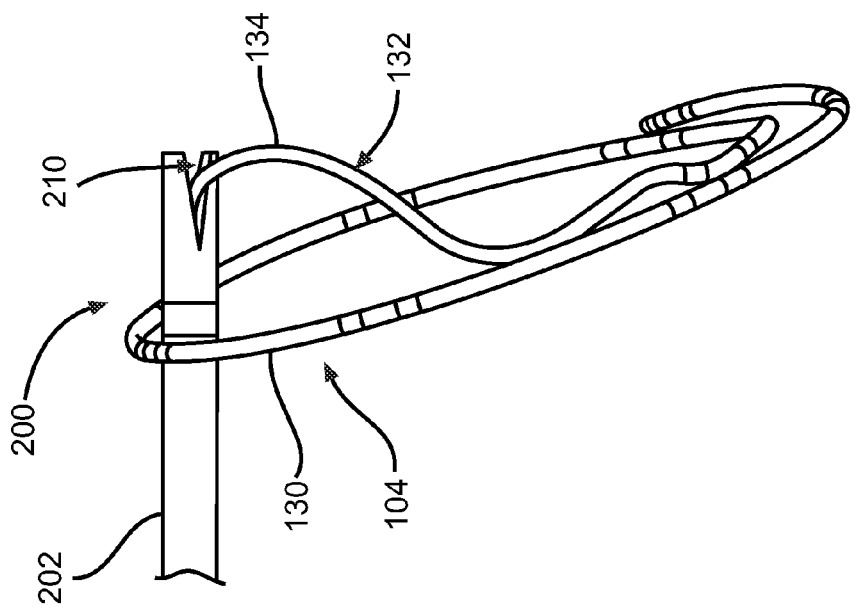

One exemplary method of manipulating a dual loop structure 104 with the guide 200 is illustrated in FIGS. 15a-15e. After being deployed adjacent to a pulmonary vein or other target tissue region, the dual loop structure 104 will be positioned distally of the tubular member 202, as is illustrated in FIG. 15a. Region 132-1 of the second loop 132 is located radially outside the first loop 130. The catheter 102 is then pulled proximally, i.e. in the direction of arrow P in FIGS. 15b and 15c. When the catheter 102 reaches the position illustrated in FIG. 15b, a portion of the first loop 130 will be wedged into the indentation 210 and a portion of the second loop 132, including region 132-1, will be located within the tubular member 202. When the catheter 102 reaches the position illustrated in FIG. 15c, the portion of the first loop 130 will remain be wedged into the indentation 210 and a larger portion of the second loop 132 will be located within the tubular member 202. The various bending forces acting on the portion of the second loop 132 that remains outside the tubular member 202 cause this portion of the second loop to distort in the manner illustrated in FIG. 15c.

Figure 15D:
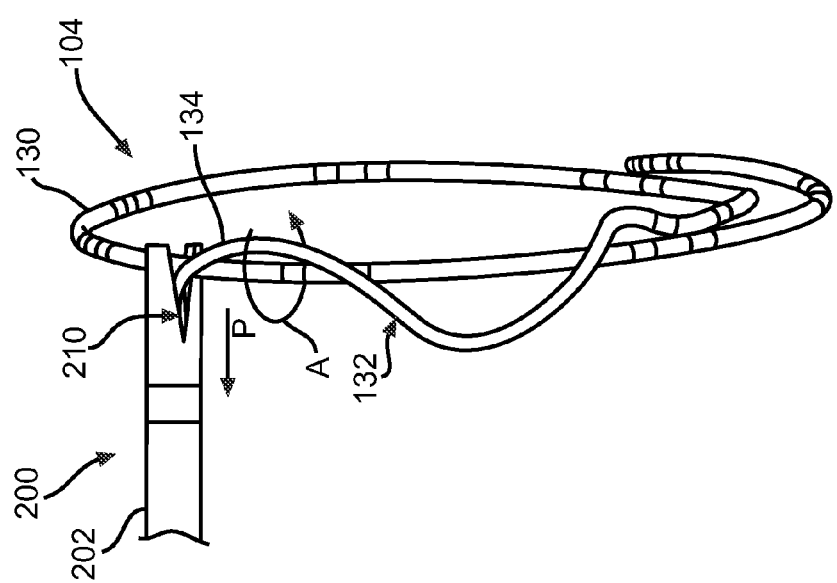

The portion of the dual loop structure 104 that defines the second loop 132 remains radially outside the first loop 130 in the orientations (or "states") illustrated in FIGS. 15b and 15c. However, in the state illustrated in FIG. 15c, the portion of the dual loop structure 104 that defines the second loop apex 134 is adjacent to the first loop 130 and is being urged radially inwardly by the bending forced acting thereon. Additional movement of the catheter 102 in the proximal direction (note arrow P) will cause the portion of the dual loop structure 104 that defines the second loop apex 134 to snap over and under the first loop 130 (note arrow A) such that this portion of the second loop 132 will be located radially within the first loop, as is illustrated in FIG. 15d. At this point, the various bending forces acting on the first loop 130 will urge the first loop out of the indentation 210 and over the distal end of the tubular member 202, as is also illustrated in FIG. 15d.

Figure 15E:
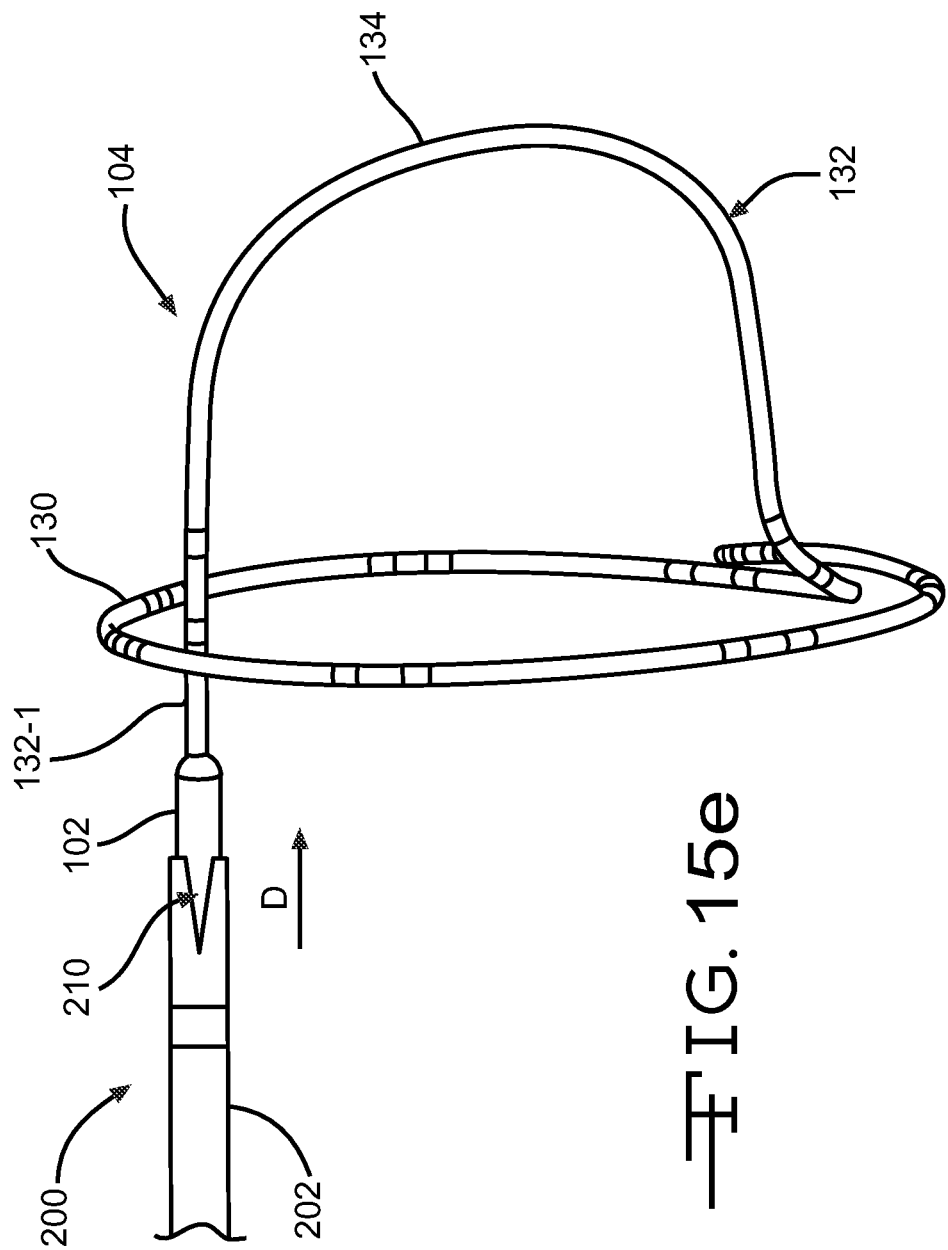

Next, the catheter 102 may be urged distally (note arrow D) until the entire dual loop structure 104 is outside the tubular member 202, as is illustrated in FIG. 15e. The dual loop structure 104 will assume essentially the same orientation that it did in FIG. 15a. Region 132-1 of the second loop 132 is, however, now located radially inside the first loop 130. The second loop 132 is also centered relative to the first loop 130.

Although the present inventions have been described in terms of the preferred embodiments above, numerous modifications and/or additions to the above-described preferred embodiments would be readily apparent to one skilled in the art. By way of example, but not limitation, the present inventions are also applicable to surgical probes. It is intended that the scope of the present inventions extend to all such modifications and/or additions and that the scope of the present inventions is limited solely by the claims set forth below.

We claim:

1. An apparatus, comprising:
   an elongate body defining a longitudinal axis, a distal region and a distal end, the distal region being movable between a substantially linear orientation and a dual loop orientation where the distal region defines a first loop that is transverse to the longitudinal axis and a second loop that is transverse to the first loop, the first loop defining a central axis that is offset from the longitudinal axis and the second loop defining a second loop apex that is distal of the first loop and first and second proximal ends that are on opposite sides of the apex; and
   a plurality of operative elements supported on the distal region of the elongate body.

2. An apparatus as claimed in claim 1, wherein the elongate body includes a catheter defining a distal end and a dual loop structure associated with the distal end of the catheter, the dual loop structure defining the distal region of the elongate body.

3. An apparatus as claimed in claim 1, wherein the first loop comprises an at least substantially full loop.

4. An apparatus as claimed in claim 1, wherein the second loop comprises an at least partial loop.

5. An apparatus as claimed in claim 1, wherein
   the first loop is substantially perpendicular to the longitudinal axis; and
   the second loop is substantially perpendicular to the first loop.

6. An apparatus as claimed in claim 1, wherein the distal end of the elongate body is proximal to the second loop apex when the distal region is in the dual loop orientation.

7. An apparatus as claimed in claim 6, wherein the distal end of the elongate body is part of the first loop when the distal region is in the dual loop orientation.

8. An apparatus as claimed in claim 1, wherein the distal region is pre-shaped to the dual loop orientation.

9. An apparatus as claimed in claim 8, wherein the distal region includes a core wire and an electrically non-conductive outer member.

10. An apparatus as claimed in claim 1, wherein the operative elements comprise electrodes.

11. An apparatus as claimed in claim 1, wherein the operative elements are arranged in a plurality of spaced operative element pairs.

12. An apparatus as claimed in claim 1, wherein
   a plurality of the operative elements are positioned about the first loop; and
   at least one of the operative elements is positioned on the second loop such that it will be distal of the first loop when the distal region is in the dual loop orientation.

13. An apparatus as claimed in claim 1, further comprising:
   a steering center support mounted proximal to the distal region; and
   at least one steering wire secured to the steering center support.

14. An apparatus as claimed in claim 1, further comprising:
   an elongate tubular body defining a distal end, an inner lumen that extends to the distal end and is configured to receive the elongate body, and an indentation extending proximally from the distal end.

15. An apparatus as claimed in claim 14, wherein the indentation is substantially V-shaped.

16. An apparatus as claimed in claim 1, wherein the first proximal end of the second loop is adjacent to a first portion of the first loop and the second proximal end of the second loop is adjacent to a second portion of the first loop.

17. An apparatus as claimed in claim 1, wherein the first and second proximal ends are offset from the first loop central axis by a substantial distance.

18. An apparatus, comprising:
   an elongate body defining a longitudinal axis, a distal region and a distal end, the distal region being movable between a substantially linear orientation and a dual loop orientation including a proximal loop and a distal loop, the distal end defining a portion of the proximal loop and the distal loop defining a distal loop apex and first and second proximal ends that are on opposite sides of the apex and proximal of the apex;
   a plurality of operative elements, on the distal region of the elongate body at fixed locations along the longitudinal axis, that will be positioned about the proximal loop when the distal region is in the dual loop orientation; and
   at least first and second additional operative elements, on the distal region of the elongate body at a fixed location along the longitudinal axis, that will be respectively positioned on the distal loop adjacent the first and second proximal ends and distal of the proximal loop when the distal region is in the dual loop orientation, wherein the at least first and second additional operative elements are positioned on the distal loop such that they are configured to contact tissue when the distal loop is disposed within a body lumen.

19. An apparatus as claimed in claim 18, wherein the proximal loop is transverse to the longitudinal axis and the distal loop is transverse to the proximal loop and the distal loop apex is distal of the first loop.

20. An apparatus as claimed in claim 18, wherein the elongate body includes a catheter defining a distal end and a dual loop structure associated with the distal end of the catheter, the dual loop structure defining the distal region of the elongate body.

21. An apparatus as claimed in claim 18, wherein the proximal loop comprises an at least substantially full loop.

22. An apparatus as claimed in claim 18, wherein the distal loop comprises an at least partial loop.

23. An apparatus as claimed in claim 18, wherein
   the proximal loop is substantially perpendicular to the longitudinal axis; and
   the distal loop is substantially perpendicular to the proximal loop.

24. An apparatus as claimed in claim 18, wherein the distal region is pre-shaped to the dual loop orientation.

25. An apparatus as claimed in claim 24, wherein the distal region includes a core wire and an electrically non-conductive outer member.

26. An apparatus as claimed in claim 18, wherein the operative elements comprise mapping electrodes.

27. An apparatus as claimed in claim 18, wherein the operative elements are arranged in a plurality of spaced mapping electrode pairs.

28. An apparatus as claimed in claim 18, further comprising:
- a steering center support mounted proximal to the distal region; and
- at least one steering wire secured to the steering center support.

29. An apparatus as claimed in claim 18, further comprising:
- an elongate tubular body defining a distal end, an inner lumen that extends to the distal end and is configured to receive the elongate body, and an indentation extending proximally from the distal end.

30. An apparatus as claimed in claim 29, wherein the indentation is substantially V-shaped.

31. An apparatus as claimed in claim 18, wherein
- the distal region of the elongate body comprises a single tube defining an outer surface;
- the plurality of operative elements are on the outer surface of the single tube; and
- the at least first and second additional operative elements are on the outer surface of the single tube.

* * * * *

UNITED STATES PATENT AND TRADEMARK OFFICE
CERTIFICATE OF CORRECTION

PATENT NO. : 8,798,706 B2  
APPLICATION NO. : 12/561527  
DATED : August 5, 2014  
INVENTOR(S) : Kim et al.

Page 1 of 1

It is certified that error appears in the above-identified patent and that said Letters Patent is hereby corrected as shown below:

In the Specification:

Column 5  
Line 33: after "between about 55°C", delete "."  
Line 33: after "and 70°C", delete "."

Signed and Sealed this  
Twenty-first Day of October, 2014

Michelle K. Lee  
*Deputy Director of the United States Patent and Trademark Office*